United States Patent
Pallikaris et al.

(10) Patent No.: US 12,427,012 B2
(45) Date of Patent: Sep. 30, 2025

(54) DEVICES FOR RECONSTRUCTION OF A LENS CAPSULE AFTER CATARACT SURGERY

(71) Applicants: Ioannis Pallikaris, Maleviziou (GR); Onurcan Sahin, Istanbul (TR); Harilaos Ginis, Megara (GR)

(72) Inventors: Ioannis Pallikaris, Maleviziou (GR); Onurcan Sahin, Istanbul (TR); Harilaos Ginis, Megara (GR)

(73) Assignee: EYE-PCR B.V., Amsterdam (NL)

( * ) Notice: Subject to any disclaimer, the term of this patent is extended or adjusted under 35 U.S.C. 154(b) by 0 days.

(21) Appl. No.: 18/452,633

(22) Filed: Aug. 21, 2023

(65) Prior Publication Data

US 2023/0390048 A1    Dec. 7, 2023

Related U.S. Application Data

(63) Continuation of application No. 17/529,894, filed on Nov. 18, 2021, now Pat. No. 11,730,586, which is a continuation of application No. 16/216,142, filed on Dec. 11, 2018, now Pat. No. 11,213,384, which is a continuation-in-part of application No. 15/446,121, filed on Mar. 1, 2017, now Pat. No. 10,548,719.

(51) Int. Cl.
*A61F 2/16* (2006.01)

(52) U.S. Cl.
CPC .......... *A61F 2/1645* (2015.04); *A61F 2/1694* (2013.01); *A61F 2002/1683* (2013.01); *A61F 2002/169* (2015.04); *A61F 2002/16901* (2015.04); *A61F 2002/16902* (2015.04); *A61F 2002/16903* (2015.04); *A61F 2230/0013* (2013.01); *A61F 2250/0097* (2013.01)

(58) Field of Classification Search
CPC ............ A61F 2/1694; A61F 2002/1682; A61F 2002/169; A61F 2002/16901; A61F 2002/16902; A61F 2002/0091
See application file for complete search history.

(56) References Cited

U.S. PATENT DOCUMENTS

| | | | | |
|---|---|---|---|---|
| 2013/0304206 A1* | 11/2013 | Pallikaris | .............. | A61F 2/1694 623/6.43 |
| 2016/0000558 A1* | 1/2016 | Honigsbaum | ......... | A61F 2/1648 623/6.11 |
| 2016/0310264 A1* | 10/2016 | Akura | .................... | A61F 2/1635 |
| 2016/0317286 A1* | 11/2016 | Brady | ................... | A61F 2/1648 |
| 2017/0172732 A1* | 6/2017 | Liu | ....................... | A61F 2/1624 |

* cited by examiner

*Primary Examiner* — Javier G Blanco
(74) *Attorney, Agent, or Firm* — Benjamin Aaron Adler

(57) ABSTRACT

Provided herein are devices used to reconstruct a natural lens capsule after a cataract surgery. The device has a ring-shaped rigid component, a ring-shaped flexible component and a groove disposed on an inner surface of the rigid component. The rigid component has a distal end attached to the ring-shaped flexible component and a proximal end that lies against Wieger's ligament when fitted within the natural lens capsule. The ring-shaped flexible component has a proximal end that is attached to the distal end of the rigid component and a distal end that contacts an anterior surface of the natural lens capsule when fitted therein. The groove is disposed to receive optics of an intraocular lens and/or the ledge is disposed to secure haptics thereof.

6 Claims, 12 Drawing Sheets

FIG. 14A
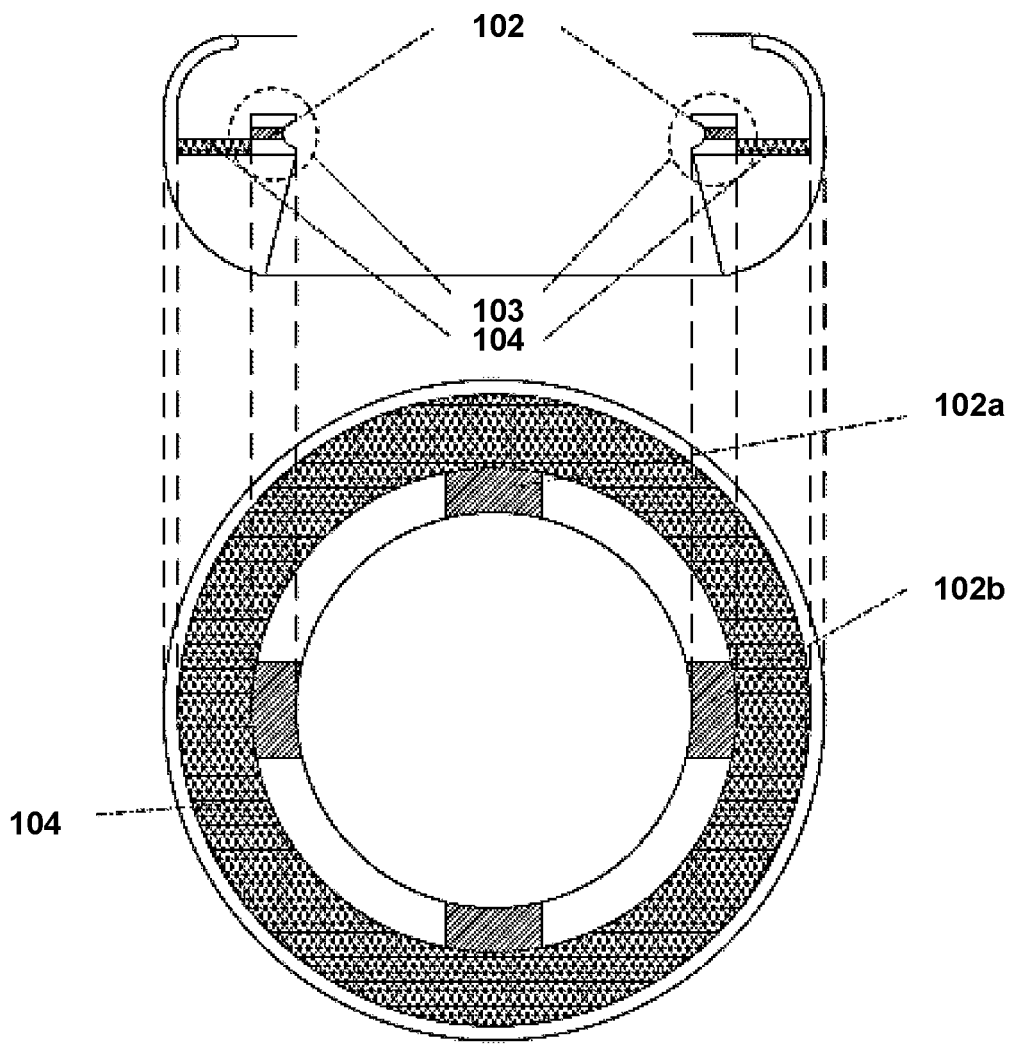
FIG. 14B
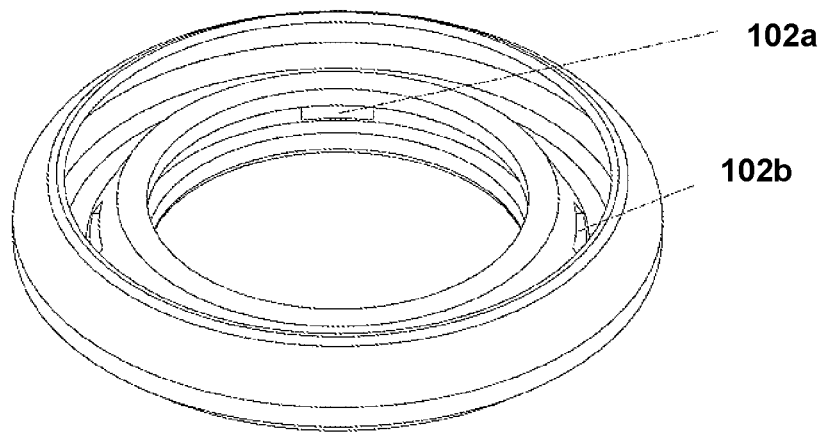
FIG. 14C

FIG. 15A
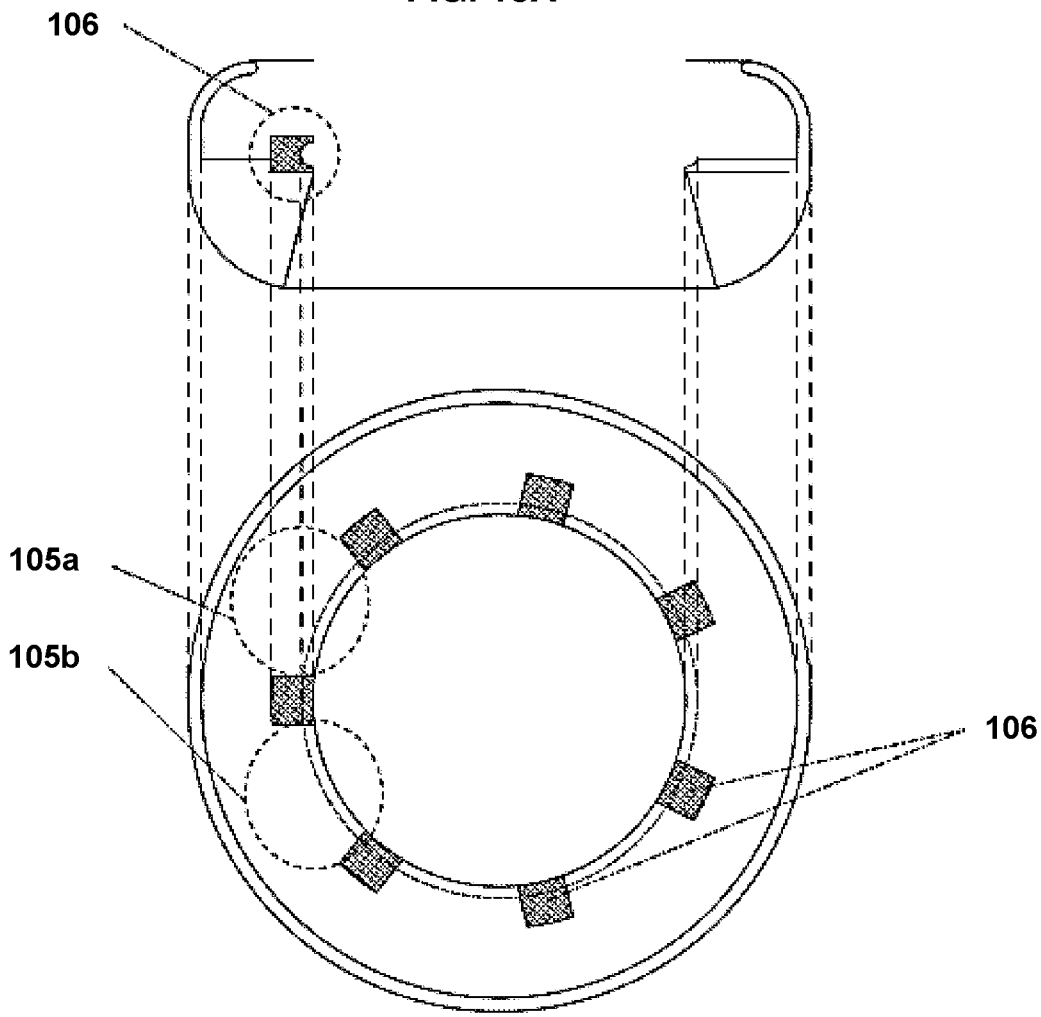
FIG. 15B
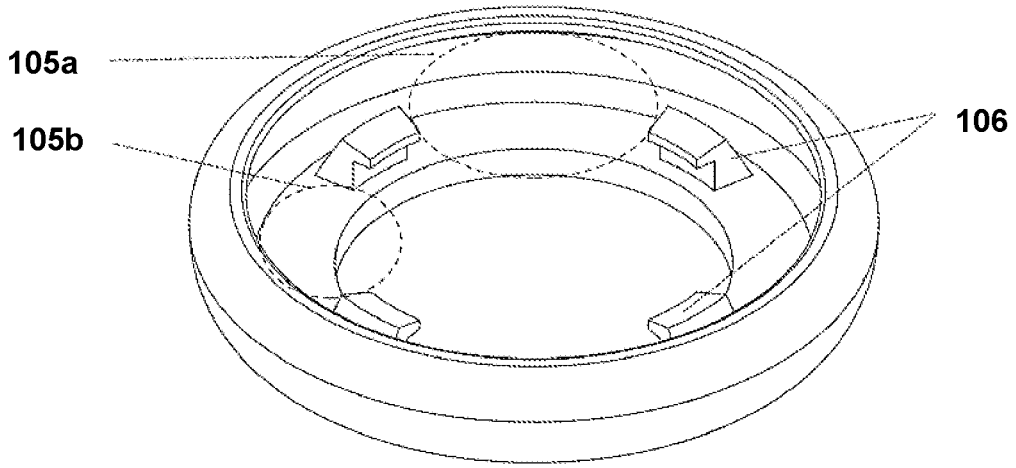
FIG. 15C

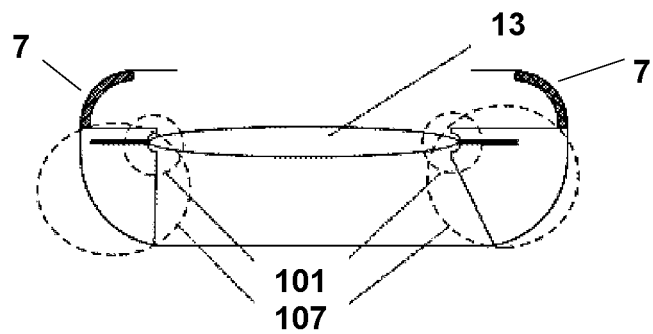
FIG. 16
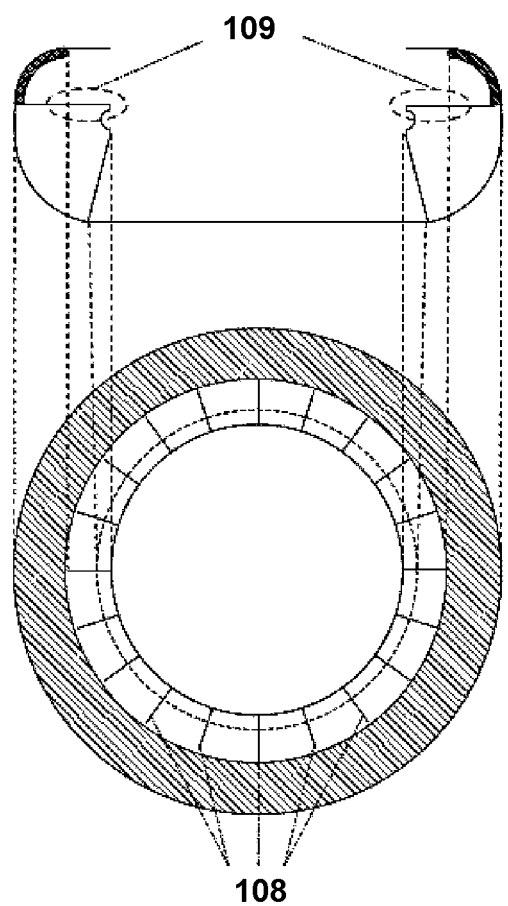
FIG. 17A
FIG. 17B

DEVICES FOR RECONSTRUCTION OF A LENS CAPSULE AFTER CATARACT SURGERY

CROSS-REFERENCE TO RELATED APPLICATION

This application is a continuation under 35 U.S.C. § 120 of pending application of U.S. Ser. No. 17/529,894, filed Nov. 18, 2021, which is a continuation under 35 U.S.C. § 120 of U.S. Ser. No. 16/216,142, filed Dec. 11, 2018, now U.S. Pat. No. 11,213,384, which is a continuation-in-part application under 35 U.S.C. § 120 of non-provisional application U.S. Ser. No. 15/446,121, filed Mar. 1, 2017, now U.S. Pat. No. 10,548,719, the entirety of all of which is hereby incorporated by reference.

BACKGROUND OF THE INVENTION

Field of the Invention

The present invention relates to the fields of ophthalmology and surgical devices for operations on the eye. More specifically, the present invention relates to a device for functional and anatomical reconstruction of human lens capsules and for precise placement of an intraocular lens for any surgery that requires replacement and alignment of the crystalline lens.

Description of the Related Art

An intraocular lens is a plastic lens that has substantially the same optical power as a natural lens it is intended to replace. Typically, during a cataract surgery, an ophthalmic surgeon removes a cataract impaired natural lens and replaces it with an artificial intraocular lens. There are generally three types of intraocular lenses including refractive lenses, diffractive lenses, and refractive-diffractive lenses. A refractive lens converges light towards a focal point on the optical axis by refraction, while a diffractive lens creates a diffraction pattern forming one focal point on the optical axis per diffraction order. A refractive-diffractive lens combines the features of both types. However, these purely refractive bi- or multi-focal lenses have some notable drawbacks. Firstly, their effectiveness is heavily dependent on the size and the centration of the pupil. Secondly, because they have several focal points, the resulting contrast is reduced. This may induce the formation of halos, in particular, in far vision, with reduced luminosity (see, for example, U.S. Pat. No. 8,636,796 B2).

Moreover, posterior capsule opacification (PCO or after cataract) remains a common problem after cataract surgery with implantation of an intraocular lens. Posterior capsule opacification generally results from the transition from intracapsular cataract extraction (ICCE) to extracapsular cataract extraction (ECCE), where the posterior lens capsule is left intact during surgery. Patients with posterior capsule opacification suffer from decreased visual acuity, impaired contrast sensitivity, and glare disability. Clinically, components of posterior capsule opacification are identified as a regeneratory component and a fibrotic component with a regeneratory posterior capsule opacification component much more common than the fibrotic component.

Regenerative posterior capsule opacification results from residual lens epithelial cells (LECs) from the lens equator region, the so-called E-cells, migrating and proliferating into the space between the posterior capsule and the intraocular lens and forming layers of lens material and Elschnig pearls. In contrast, fibrotic posterior capsule opacification is caused by lens epithelial cells from the anterior capsule that undergo transformation to myofibroblasts and gain access to the posterior capsule, causing whitening and wrinkling of the capsule. This can lead to decentration of the intraocular lens and hinder visualization of the peripheral retina. Findl et al. (J Cataract Refract Surg 2003; 29(1):106-11) disclose that both components of posterior capsule opacification lead to a decrease in visual function when they affect the central region around the visual axis. A YAG or Nd laser, utilized in a YAG laser capsulotomy, is most commonly used to treat posterior capsule opacification. However, as disclosed in Georgalas et al. (Ther Clin Risk Manag. 2009; 5:133-137) laser capsulotomy may lead to other complications, such as retinal detachment or intraocular pressure rise.

European Patent No. 507292B1 describes the need of an "inhibiting device" for keeping the shape of the capsular bag substantially circular after a cataract extraction and inhibiting issues such as invasion of metamorphosed epithelial cells into a posterior capsular bag and further to inhibiting device wherein an intraocular lens can be retained in good state by forming a groove in the inner periphery thereof. He describes a steady circular shape of the device effective to inhibit capsular shrinking without referring to the actual diameter of the outer part of the ring.

US Publication No. 2006/0047339 A1 describes a device attached to natural lens capsule such that the lens capsule may be maintained in a configuration to avoid post-operative changes that are deleterious to vision. Single or dual optics system is provided, which may be accommodating. The role of the "postoperative contraction" of the empty capsule, in the displacement of the lens, resulting in optical changes and in induced astigmatism is emphasized. Therefore, there is a need to provide a device or apparatus and procedure to maintain the form of the lens capsule and to maintain the diameter a capsulotomy opening for the device.

International Publication No. WO 2007/044604 A1 describes the "spatial relationship of structures within the eye, such as the distance from the a surface of the cornea to a posterior surface of the crystalline lens capsule and from the cornea or the posterior surface of the lens capsule" to the retina is measured preoperatively, for example by using ultrasound, partial coherence interferometry, optical coherence tomography or laser measuring techniques or by any other means known to the art, thus establishing the preoperative anatomical relationships. A surgical procedure, such as an intraocular lens implantation is performed, and spacing means are provided to restore those premeasured spatial relationships or a predetermined new spacing. The spacing means may include, for example spacers, rings, inflatable structures or thick or multiple lenses. These means help with maintaining the normal depth of the patient's anterior and posterior capsule and prevent forward movement of the vitreous and retinal detachment that may occur as a result of such movement.

Goldberg (Clin Ophthalmol. 2011; 5:1-7) states that "the crossing zonules cradle, shape stabilize the posterior lens. In the model, the anterior vitreous zonule is inserted in the Wieger's ligament, and the PIZ-LE zonule anchors the lens equator to the posterior insertion zone. The crossing zonules and Wieger's ligament maintain lens placement while the anterior and posterior zonules provide reciprocal accommodation and disaccommodation. Wieger's ligament representing the mid-peripheral zone of the posterior capsule is the most important area for stabilizing the lens position during the accommodation.

U.S. Publication No. 2010/0204790 A1 describes an intraocular lens device having a ring shape fixation platform, which can create a "frame" in which the intraocular lens of the present invention can be attached . . . and conclude the discovery of the present invention makes possible a surgical method for insertion and subsequent removal and exchange of an intraocular lens with reduced risk of injury to the eye or loss of sight.

Based on the Market Scope Report (2015 Comprehensive Report on the Global Intraocular Lens Market, June 2015), the premium intraocular lens market is going to reach the 9.3% of the global number and the 34% of the total revenues of the global intraocular lens market. The multifocal and Toric IOLs will dominate the premium intraocular lens market at the market share of almost 90%. Toric and multifocal are very sensitive to the exact centration and positioning inside the capsule.

Several patents and publications, including U.S. Pat. No. 9,339,375 B2, U.S. Pat. No. 4,710,194, U.S. Publication No. 2005/0085,907, U.S. Publication No. 2005/0209692, U.S. Publication No. 2010/0204790, U.S. Publication No. 2010/0228344, U.S. Publication No. 2011/0082543 and European Application No. 037,390 A2, disclose a variety of intracapsular rings for different purposes. However, these works describe rings that either have one standard size or a variety of sizes without any adjustability for accommodation. These devices generally comprise a ring and an optical system adapted to the ring. Some of the devices comprise a deformable ring that under the pressure of the ciliary body changes the shape of the central optical part and mimics an accommodation mechanism.

None of the previous works in the field take into consideration the modern theory of accommodation and the preservation of continuous change of the shape of the capsule, due to the complexity of zonular traction regarding the multifocal and toric intraocular lens, which are already in the market and expected to improve rapidly in the near future. Therefore, there is a recognized need in the art for a device and method for reconstructing the capsule. Particularly, the prior art is deficient in devices that enable precise placement and alignment of the intraocular lens post-surgically. The present invention fulfills this long-standing need and desire in the art.

SUMMARY OF THE INVENTION

The present invention is directed to a device for reconstructing a natural lens capsule of an eye after a cataract surgery. The device comprises a ring-shaped rigid component, a ring-shaped flexible component and a groove disposed on an inner surface of the rigid component. The rigid component comprises a distal end and a proximal end configured to contact a Wieger's ligament in the eye. The ring-shaped flexible component comprises a proximal end that is attached to the distal end of the rigid component, and a distal end disposed to contact with an anterior surface of a natural lens capsule. The groove is disposed on an inner surface of the rigid component and configured to receive optics on an intraocular lens. In a related invention, the device further comprises a ledge that is formed on an inner surface of the ring-shaped flexible component and is configured to secure haptics of the intraocular lens.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

FIGS. 14A-14C show a cross-sectional, top and perspective view of the device. FIG. 14A is a cross-sectional view from the side of the device showing the rigid component and a continuous ring-shaped groove. FIG. 14B is a top view of the device showing a plurality of slits along the continuous ring-shaped groove. FIG. 14C is a front to back perspective view of the device showing a plurality of slits along the continuous ring-shaped groove.

FIGS. 15A-15C show a cross-sectional, top and perspective view of the device. FIG. 15A is a cross-sectional view from the side of the device showing a discontinuous ring-shaped groove. FIG. 15B is a top view of the device showing a plurality of openings disposed along the discontinuous ring-shaped groove. FIG. 15C is a front to back perspective view of the device showing the plurality of openings disposed along the discontinuous ring-shaped groove.

FIG. 16 is a cross-sectional view of the device showing an asymmetric rigid component, a flexible component and optics of an intraocular lens secured in a ring-shaped groove disposed on an inner surface of the rigid component.

FIGS. 17A-17B show a cross-sectional and a top view of the device. FIG. 17A is a cross-sectional view from the side of the device showing a symmetric rigid component and a flexible component. FIG. 17B is a top view of the device showing a plurality of markers disposed on a top surface of the rigid component.

FIG. 19A is a cross-sectional view of the device showing a rigid component constructed of an inner part that secures the optics and/or haptics of an intraocular lens and a concentric outer part that holds the inner part in position. FIG. 19B is a cross-sectional view of the device showing a rigid component constructed of an inner part that secures the optics and/or haptics of an intraocular lens and a non-concentric outer part that holds the inner part in position.

FIG. 20A is a cross-sectional view from the side of the device showing a flexible component and a rigid component comprising an inner part and an outer part. FIG. 20B is a top view of the device showing a plurality of markers disposed at the distal end of the inner part and the outer part.

DETAILED DESCRIPTION OF THE INVENTION

Figure 1:
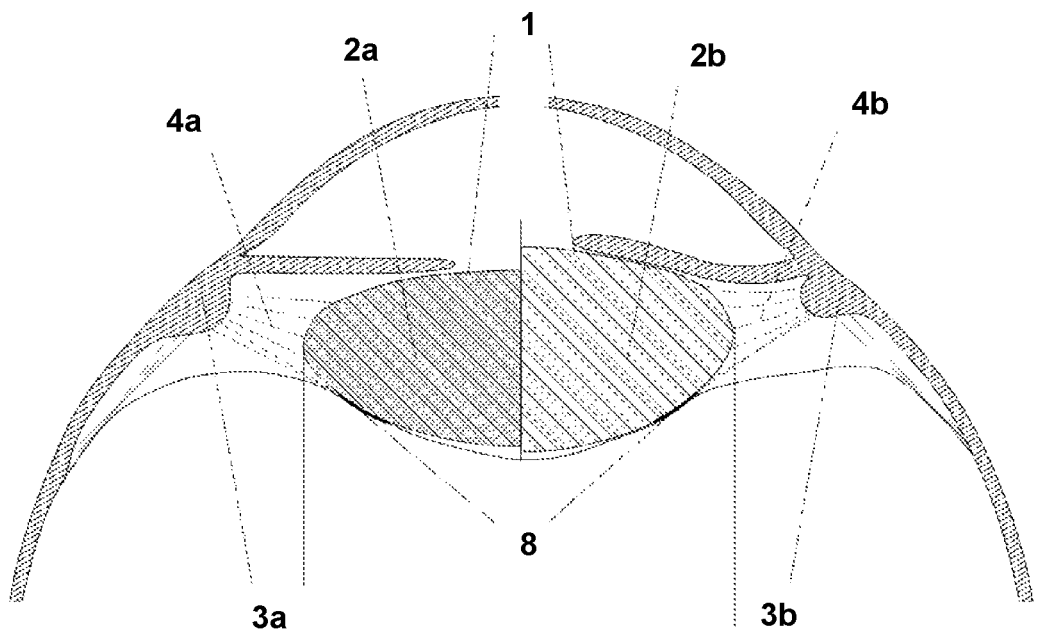
FIG. 1 depicts the structure of a capsule and Wieger's ligament with (left side) and without (right side) contraction of ciliary body.

As used herein, the following terms and phrases shall have the meanings set forth below. Unless defined otherwise, all technical and scientific terms used herein have the same meaning as commonly understood to one of ordinary skill in the art.

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof. The terms "comprise" and "comprising" are used in the inclusive, open sense, meaning that additional elements may be included.

As used herein, the term "or" in the claims refers to "and/or" unless explicitly indicated to refer to alternatives only or the alternatives are mutually exclusive, although the disclosure supports a definition that refers to only alternatives and "and/or".

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the term "distal end" refers to an end that is away from the posterior surface of the capsule; the term "proximal end" refers to an end that is toward the posterior surface of the capsule.

As used herein, the term "sharp" refers interchangeably to "tapering to an edge" or "tapered".

In one embodiment of the present invention, there is provided a device for reconstructing a natural lens capsule of an eye after a cataract surgery, comprising a ring-shaped rigid component comprising: a distal end in contact with an anterior surface of the capsule; and a proximal end disposed against a Wieger's ligament in the eye; a ring-shaped flexible component substantially concentric with the rigid component and flexibly fitted against an inner surface of the capsule, comprising: a proximal end formed on an outer surface of the proximal end of the rigid component; and a distal end extending away from the rigid component; and a groove disposed on an inner surface of the rigid component configured to receive haptics on an intraocular lens.

Further to this embodiment the device may comprise a ledge formed from a top of the distal end of the rigid component. In this further embodiment, the ledge may comprise a plurality of markers disposed on a top surface thereof, configured to guide a toric lens alignment. Also in this embodiment the ledge may have a width of about 0.1 mm to about 1 mm wide.

In both embodiments, the proximal end of the rigid component may have a thickness of about 0.2 mm to about 1 mm. Also, the distal end of the rigid component may have a thickness of about 0.1 mm to about 0.5 mm. In addition, the rigid component may be made of or may comprise, but are not limited to, silicon, acryl, poly(methyl methacrylate), hydrogel, or a combination thereof.

Also in both embodiments, the ring-shaped rigid component may be substantially perpendicular in relation to an anterior surface of the natural lens capsule when fitted inside. In both embodiments the ring-shaped flexible component may be configured to flex away from the rigid component, when ciliary muscles are relaxed and zonules are tense, and to flex toward the rigid component, when the ciliary muscles are contracted and the zonules are relaxed.

Further to both embodiments, the ring-shaped flexible component may comprise a plurality of gaps disposed around a circumference thereof. Also, the gaps each may have a width of about 0.1 mm to about 5 mm. In addition, the ring-shaped flexible component may have a thickness of about 0.05 mm to about 0.75 mm. Furthermore, the ring-shaped flexible component may be made of or may comprise, but are not limited to, silicon, acryl, poly(methyl methacrylate), hydrogel, or a combination thereof. Further still in this embodiment, the ring-shaped rigid component and the ring-shaped flexible component form an angle of about 2 degree to about 90 degree when fitted inside the natural lens capsule.

In another embodiment of the present invention, there is provided a device for flexibly restoring tension for a natural lens capsule after a cataract surgery, comprising: a ring-shaped rigid component comprising: a distal end disposed in a supporting relationship with an anterior surface of the capsule and; a proximal end disposed in a supporting relationship with an posterior surface of the capsule and disposed against a Wieger's ligament of the eye; and a ledge formed from a top of the distal end of the rigid component; a ring-shaped flexible component substantially concentric with the rigid component and flexibly fitted against an inner surface of the capsule, configured to flex away from the rigid component when ciliary muscles are relaxed and zonules are tense, and flex toward the rigid component when the ciliary muscles are contract and the zonules are relaxed, the flexible component comprising: a proximal end formed on an outer surface of the proximal end of the rigid component; and a distal end extending away from the rigid component; and a groove disposed on an inner surface of the rigid component configured to receive haptics on an intraocular lens.

Further to this embodiment, the device may comprise a plurality of markers disposed on a top surface of the ledge configured to guide toric lens alignment. In another further embodiment the device may comprise a plurality of gaps disposed around a circumference of the ring-shaped flexible component configured to improve flexibility thereof. In this further embodiment, the gaps each may have a width of about 0.1 mm to about 5 mm wide.

In all embodiments, the ledge may have a width about 0.1 to about 1 mm. Also, the proximal end of the rigid component may have a thickness of about 0.2 mm to about 1 mm and the distal end of the rigid component may have a thickness of about mm to about 0.5 mm. In addition, the ring-shaped rigid component may be made of or may comprise, but are not limited to, silicon, acryl, poly(methyl methacrylate), hydrogel, or a combination thereof. Furthermore, the ring-shaped rigid component may be substantially perpendicular in relation to an anterior surface of the natural lens capsule when fitted inside. Further still, the ring-shaped rigid component and the ring-shaped flexible component form an angle of about 2 degrees to about 90 degrees when disposed inside the natural lens capsule.

In yet another embodiment of the present invention, there is provided a device for reconstructing a natural lens capsule of an eye after a cataract surgery, comprising a ring-shaped rigid component comprising a distal end and a proximal end configured to lie against a Wieger's ligament when fitted within the natural lens capsule of the eye; a ring-shaped flexible component comprising a proximal end that is attached to the distal end of the rigid component and a distal end configured to contact an anterior surface of a natural lens capsule when fitted therein and a groove disposed on an inner surface of the rigid component and configured to receive optics on an intraocular lens.

Further to this embodiment the device comprises a ledge formed on an inner surface of the flexible component and is configured to secure haptics of the intraocular lens. In this further embodiment the ledge may have a width from about 0.1 mm to about 1 mm.

In both embodiments, the ring-shaped rigid component may be made of silicon, an acrylic, a poly(methyl methacrylate), or a hydrogel or a combination thereof. Also, in these embodiments, the ring-shaped rigid component may be substantially concentric with the ring-shaped flexible component or is non-coaxial to the ring-shaped flexible component. In addition, the ring-shaped rigid component may be substantially perpendicular in relation to an anterior surface of the natural lens capsule when fitted inside. Alternatively, the distal end of the ring-shaped rigid component may be disposed at an angle to an anterior surface of the natural lens capsule when fitted inside.

Furthermore, in both embodiments the ring-shaped rigid component may comprise a plurality of markers disposed on a top surface configured to guide a toric lens alignment. Further still, the proximal end of the rigid component may be configured to have a thickness ranging from about 0.2 mm to about 1 mm, and the distal end of the rigid component may be configured to have a thickness ranging from about 0.1 mm to about 0.5 mm.

Further still in these embodiments, the ring-shaped rigid component may comprise a plurality of openings may be disposed on an inner surface thereof that are configured to reduce total volume of the ring-shaped rigid component. Further still, the ring-shaped rigid component may comprise sharp edges at the distal end.

In one aspect of both embodiments the ring-shaped rigid component may comprise an inner part and an outer part in a concentric relationship. In this aspect a relative rotational position of the inner part and the outer part may be indicated by markers placed at the distal end of both inner and outer part this is not in the claim. The inner part and outer part may be made from the same material or different materials. For example, the materials may be as described supra. In another aspect the ring-shaped rigid component may comprise an inner part and an outer part disposed in a non-coaxial relationship.

In both embodiments, the ring-shaped flexible component may be configured to flex away from the rigid component when ciliary muscles are relaxed and zonules are tense, and flex toward the rigid component when the ciliary muscles are contracted and the zonules are relaxed when fitted inside a natural lens capsule. Also, the flexible component may have any thickness from about 0.05 mm to about 0.75 mm. In addition the ring-shaped flexible component may be made of the materials as described supra.

Furthermore the flexible component may comprise a plurality of gaps disposed around a circumference. Representative gaps have a width from about 0.1 mm to about 5 mm. Further still, the rigid component and the flexible component may form an angle from about 2 degrees to about 90 degrees when fitted inside the natural lens capsule.

In addition in another aspect of both embodiments, the groove is continuous circumferentially. Further to this aspect the groove may comprise a plurality of slits disposed around the groove configured to allow passage and relaxation of haptics formed on the optics of the intraocular lens. In both of these aspects each of the plurality of slits may have a width from about 1 degree to about 180 degrees rotationally. In yet another aspect the groove is discontinuous circumferentially. Further to this aspect the groove may comprise at least one opening disposed around a circumference thereof. In both these aspects each of the openings may have a width from about 0 degrees to about 180 degrees rotationally.

Provided herein are devices for reconstruction of the capsule 1 after a cataract surgery. As described below, the invention provides a number of advantages and uses, however such advantages and uses are not limited by such description. Embodiments of the present invention are better illustrated with reference to the Figure(s), however, such reference is not meant to limit the present invention in any fashion. The embodiments and variations described in detail herein are to be interpreted by the appended claims and equivalents thereof.

As shown in FIG. 1, the lens of the eye switches between flattened 2a or convex 2b when the ciliary muscles relax or contract to adjust vision focus. More specifically, when an eye is looking at objects at a far distance, the ciliary muscles are relaxed 3a and the zonules 4a are tensed, resulting in the lens being flattened. When the ciliary muscles are contracted 3b and the zonules are relaxed 4b, the lens of the eye is in a convex shape 2b, providing more refractive power. Therefore, a concentric rings-shaped device 5 is used to accommodate the flexibility of the dynamic structure of an eye.

Figure 2:
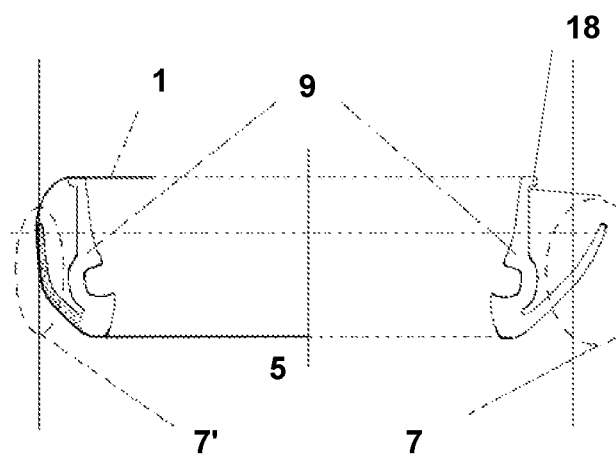
FIG. 2 is a cross-sectional view of the device showing the flexible component of the device in free form (right side) and fitted against the side surface of a capsule of an eye (left side).

As shown FIG. 2, the device has a V-shaped cross-sectional surface. The device comprises a rigid component 9 and a flexible or deformable component 7 (without tension) or 7' (with tension) disposed outside of or posterior to the rigid component. A proximal end of the flexible component is formed at the outer surface of at the proximal end of the rigid component. When it is placed in a natural lens capsule, the rigid component 9 supports the lens capsule while the flexible component 7' fits against and contacts the side surface of the lens capsule, configured to contract or relax with the contraction or relaxation of the capsule. Generally, the rigid component may be perpendicular in relation to an anterior surface of the natural lens capsule when fitted inside.

Figure 3:
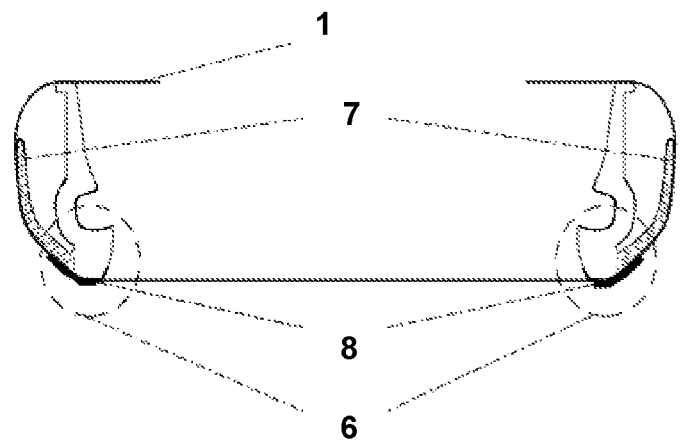
FIG. 3 is a cross-sectional view of the device showing the proximal end of the device is disposed in the capsule and against Wieger's ligament.

FIG. 3 illustrates that when the device is placed into the natural lens capsule, the proximal end of the rigid component is disposed against Wieger's Ligament 8. The outer surface of the flexible component is in direct contact with the inner surface of the capsule. The flexible component is under constant pressure from the capsule. It blocks any fibroblast and lens epithelial cells migrating to the posterior capsule. Preferably, the angle between the rigid component and the flexible component is about 0 degrees to about 90 degrees when the capsule contracts and relaxes. The rigid component and the flexible component individually may be made of biocompatible materials, such as, but not limited to, silicon, an acrylic, such as poly(methyl methacrylate), hydrogel or a combination thereof. The thickness of the rigid and flexible components define the parameters of flexibility and rigidity.

Figure 4:
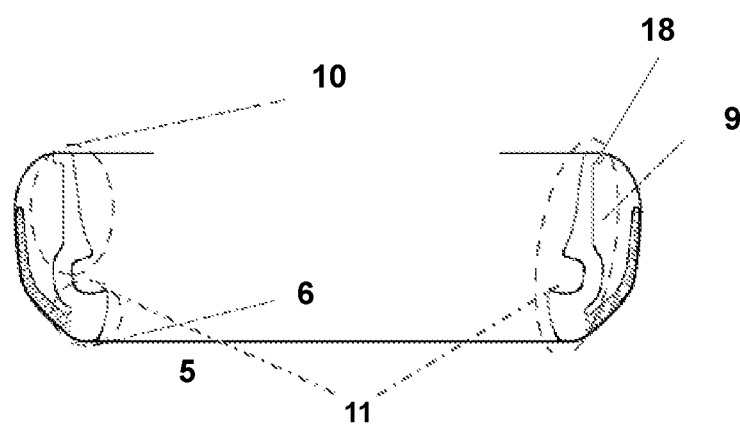
FIG. 4 is a cross-sectional view of the device showing the diameter of the anterior surface of the capsule is greater than the posterior surface thereof.

As shown in FIG. 4, the top portion 10 of the rigid component, which is in contact with the anterior of the capsule, is thinner than the bottom portion 6 thereof, which is in contact with the posterior end of the capsule. A ledge 18 is formed at the distal end of the top portion of the rigid component. The diameter of the top portion 10 of the rigid component may be greater than or substantially the same as that of the bottom portion 6 thereof. This conical-like shape of the rigid component creates a better visual field for surgeons and allows them to see the groove 11 during the eye surgery, providing easy access for placing and aligning the lens 13. Preferably, the thickness of the rigid component may be from 0.1 mm to 1 mm. The thickness of the flexible component may be from 0.05 mm to 0.75 mm.

Figure 5:
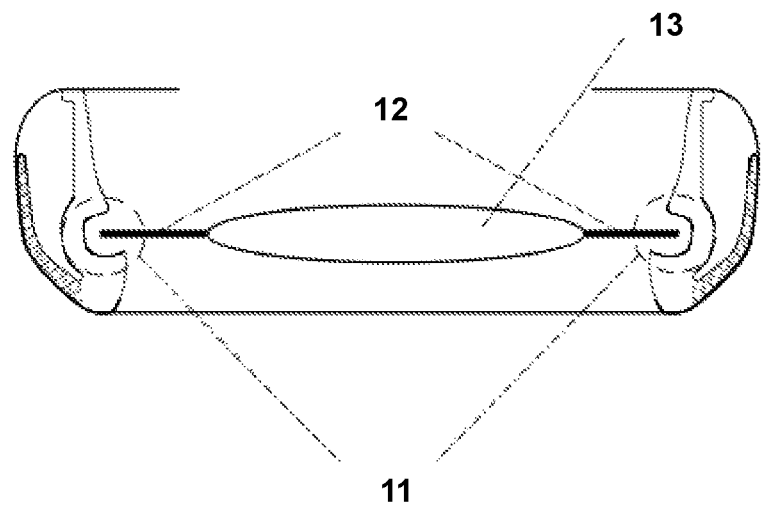
FIG. 5 is a cross-sectional view of the device showing an intraocular lens is placed in the device by inserting the haptics thereof into a groove disposed on the inner surface of the rigid component.

FIG. 5 illustrates that a ring-shaped groove 11 is disposed on the inner surface of the rigid component and is configured to fit or receive and to secure the haptics 12 on the intraocular lens. The groove 11 keeps the lens well aligned in the center of the capsule. Once the haptics 12 on the lens 13 are placed in the groove 11, the groove 11 removably secures the haptics 12 and prevents the lens 13 from tilting or twisting.

Figure 6:
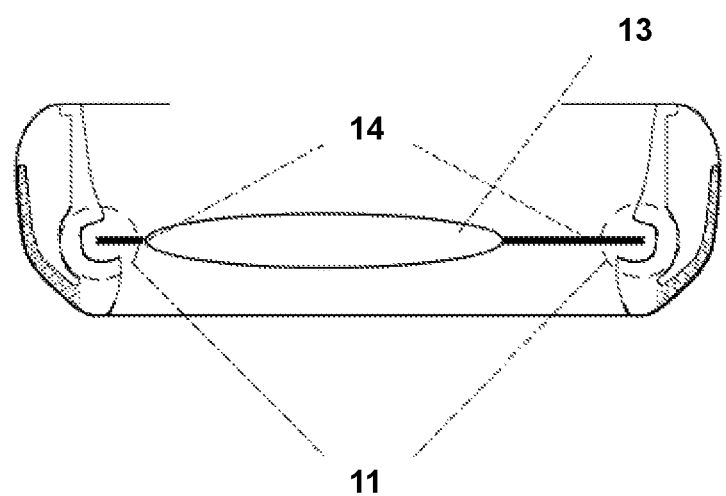
FIG. 6 is a cross-sectional view of the device showing an asymmetric intraocular lens is placed in the device.

FIG. 6 shows that an intraocular lens with asymmetric haptics 14 is placed into the ring-shaped groove 11. This is used to fit premium intraocular lens in a patient's eye with higher angle kappa, in case of a pupil eccentricity in regards to the optical axis, where this eccentricity is greater than 0.2 mm.

Figure 7:
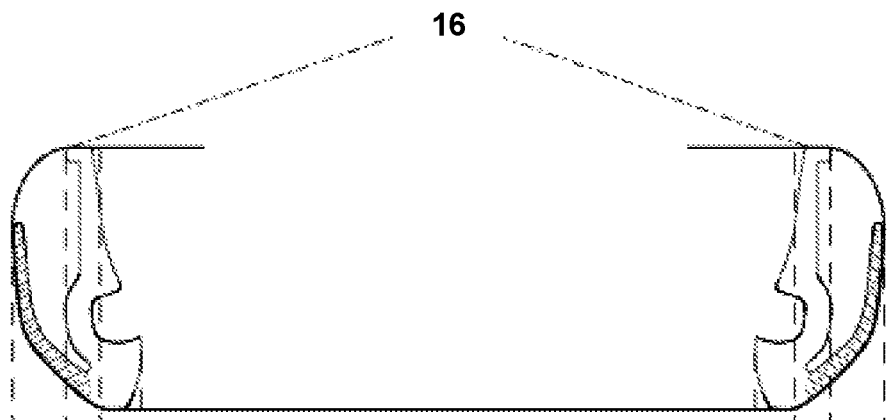
FIG. 7 is a cross-sectional view from the side of the device showing the rigid component and the flexible component.
Figure 8:
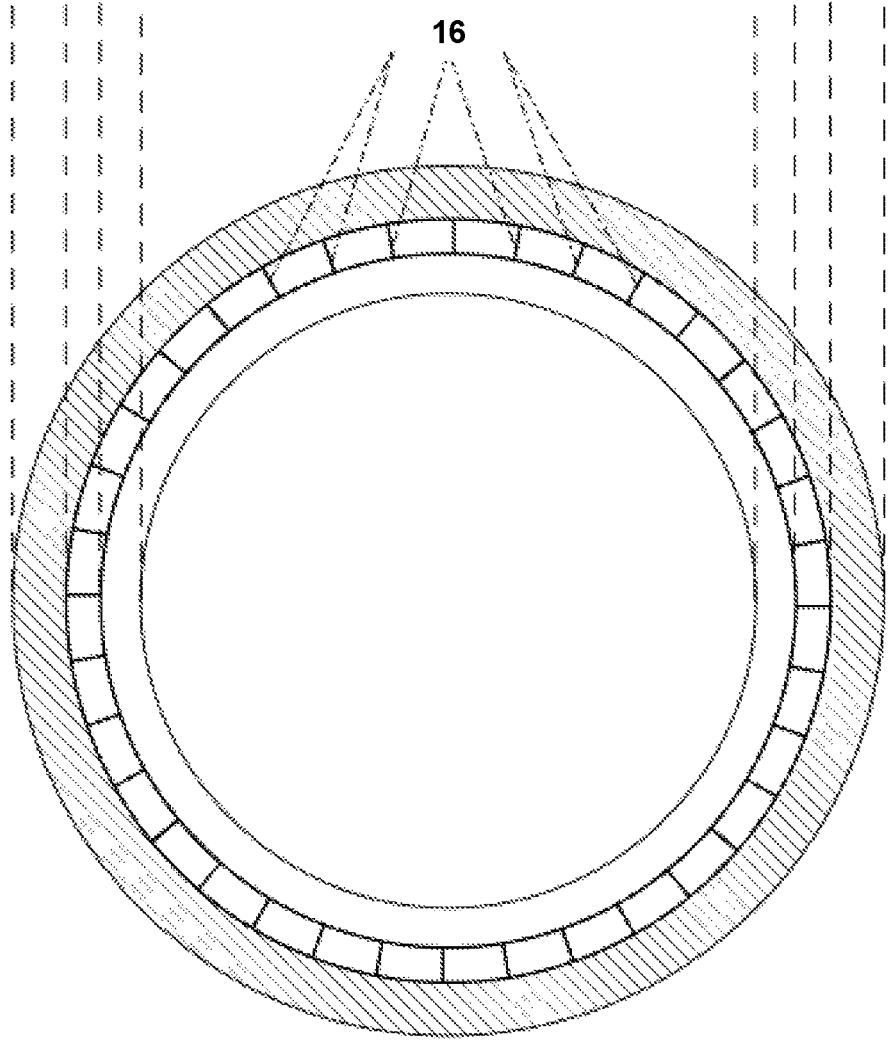
FIG. 8 is a top view of the device showing a plurality of markers as the indicators for toric intraocular lens alignment is disposed on the top surface of the rigid component.

FIG. 7 and FIG. 8 illustrate the corresponding parts in a side view shown in and a top view, respectively, of the device. Particularly, FIG. 8 shows a plurality of markers 16 disposed on the top surface of the ledge formed on the rigid component.

Figure 9:
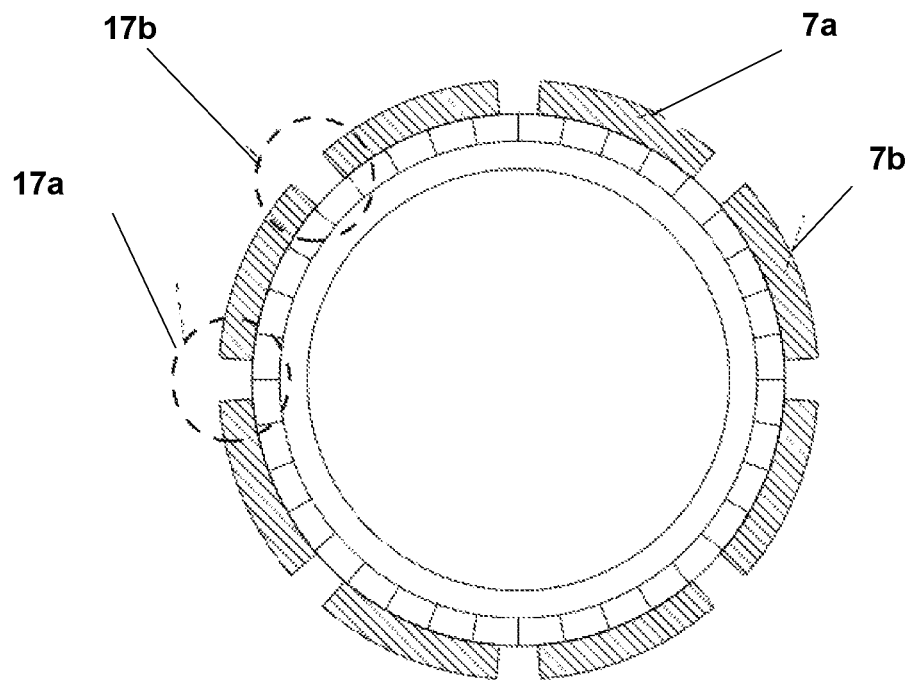
FIG. 9 is a top view of the device showing a plurality of gaps disposed along the circumference of the flexible component to improve the flexibility thereof.

In FIG. 9 a plurality of gaps, as represented by 17a and 17b, is disposed along the circumference of the flexible component to improve the flexibility thereof. These gaps divide the flexible component into plurality of discontinuous sections, as represented by 7a and 7b.

Figure 10:
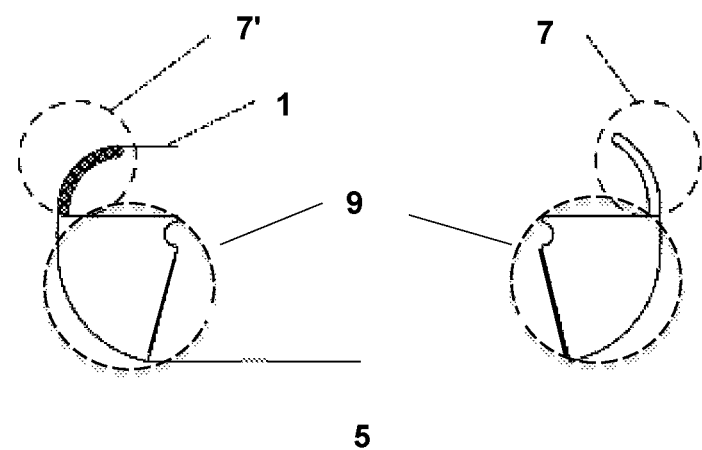
FIG. 10 is a cross-sectional view of the device showing the flexible component of the device without tension (right side) and with tension (left side) fitted distally to the rigid component.

In FIG. 10, the device 5 has a C-shaped (or Epsilon-shaped) cross-sectional surface. The device comprises a rigid component 9 and a flexible or deformable component 7 (without tension) or 7' (with tension) disposed distally to the rigid component. In this embodiment, the rigid component is substantially concentric (coaxial) in relation to the flexible component. A proximal end of the flexible component forms the upper surface of at the distal end of the rigid component. When it is placed in a natural lens capsule 1, the rigid component 9 and flexible component 7' fits against and contacts the side surface of the lens capsule. The flexible component 7' is configured to contract or relax with the contraction or relaxation of the capsule. Generally, the rigid component may be perpendicular in relation to an anterior surface of the natural lens capsule when fitted inside. The rigid component and flexible component may be made of any suitable biocompatible material including, but not limited to, silicon, poly(methyl methacrylate), acrylic and hydrogel, or a composite of two or more of these biocompatible materials. One of ordinary skill in this art would be well aware of materials that are compatible for use in the eye and may combine them in the proportions desired when manufacturing the device claimed in this invention.

Figure 11:
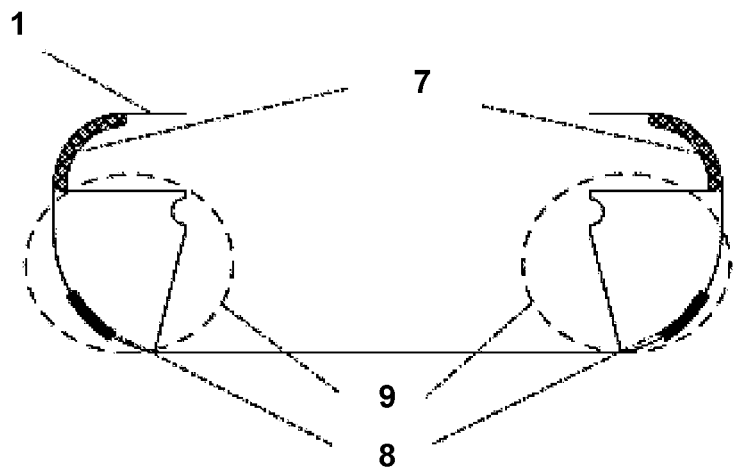
FIG. 11 is a cross-sectional view showing the device in the natural lens capsule with the proximal end of the rigid component disposed against Wieger's ligament.

With continuous reference to FIG. 10, FIG. 11 illustrates that when the device is placed into the natural lens capsule 1, the proximal end of the rigid component 10 is disposed against Wieger's Ligament 8. The outer surface of the both flexible component 11 and rigid component is in direct contact with the inner surface of the capsule. The rigid and flexible components are under constant pressure from the capsule. They block any fibroblast and lens epithelial cells migrating to the posterior capsule. Preferably, the angle between the rigid component and the flexible component is about 2 degrees to about 90 degrees when the capsule contracts and relaxes. The rigid component and the flexible component individually may be made of biocompatible materials, such as, but not limited to, silicon, an acrylic, such as poly(methyl methacrylate), hydrogel or a combination thereof. The thickness and composition of the rigid and flexible components define their parameters of flexibility and rigidity.

Figure 12:
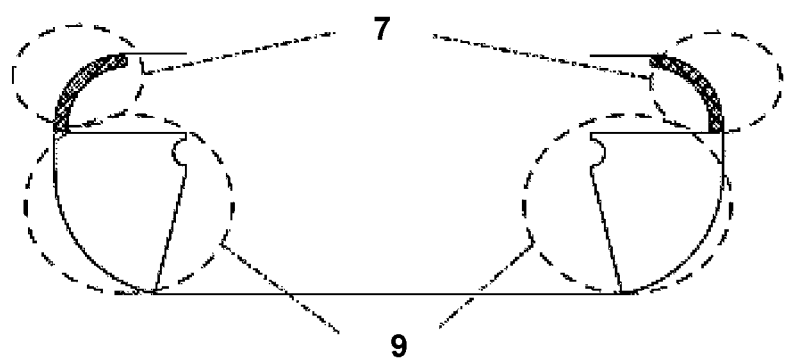
FIG. 12 is a cross-sectional view of the device showing the distal end of the flexible component, which is in contact with the anterior of the capsule
Figure 13:
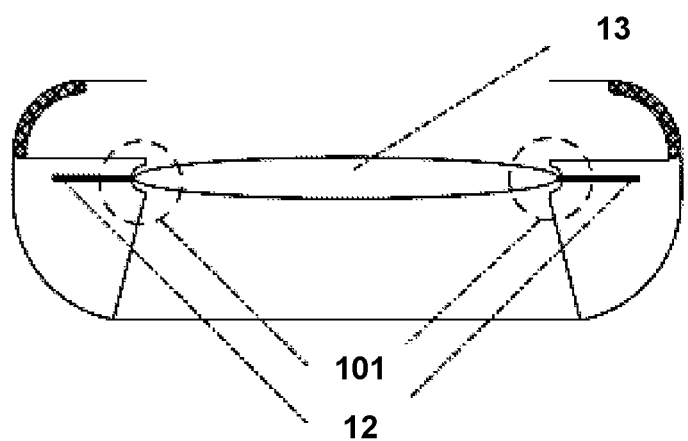
FIG. 13 is a cross-sectional view of the device showing the optics of an intraocular lens secured in a ring-shaped groove disposed on the inner surface of the rigid component.

With continuous reference to FIGS. 10 and 11, FIG. 12 illustrates the distal end of the flexible component 7, which is in contact with the anterior of the capsule, may be thinner than the bottom portion thereof, which is in contact with the equatorial part of the capsule. Preferably, the thickness of the rigid component may be from 0.1 mm to 2 mm. The thickness of the flexible component may be from 0.05 mm to 1.5 mm.

With continuous reference to FIGS. 10 to 12, FIG. 13 illustrates that a ring-shaped groove 101 is disposed on an inner surface of the rigid component and is configured to fit or receive and to secure the optics and haptics of an intraocular lens. The groove 101 keeps the lens well aligned in the center of the capsule. Once the optics of a lens 13 are placed in the groove 101, the groove 101 secures the optics and prevents the lens 13 from tilting or twisting.

FIGS. 14A and 14B illustrate a plurality of slits, represented by 102a and 102b, disposed along a continuous ring-shaped groove 103, allowing passage for haptics of an intraocular lens. Relatively these slits allow relaxation of haptics over the distal end of the rigid component 104. This relaxation is beneficial since it will ease the rotation of the intraocular lens. Once the rotational alignment is completed, fixing the optics in the groove will create stable and predictable enclosure for the intraocular lens. With continuous reference to FIGS. 14A and 14B, FIG. 14C is a front to back perspective view of the device showing the plurality of slits represented by 102a and 102b along the continuous ring-shaped groove.

FIGS. 15A and 15B illustrate a plurality of openings, represented by 105a and 105b disposed along the discontinuous ring-shaped groove 106 allowing passage for haptics of an intraocular lens. Relatively, these slits allow relaxation of the haptics over the distal end of the rigid component. With continuous reference to FIG. 15A and FIG. 15C is a front to back perspective view of the device showing the plurality of openings represented by 105a and 105b disposed along the discontinuous ring-shaped groove.

FIG. 16 illustrates an asymmetric rigid component 107 with respect to the flexible component 7. Optics of the intraocular lens 13 is placed into the ring-shaped groove 101. This is used to fit a premium intraocular lens with high angle kappa in the eye of a patient having a pupil eccentricity greater than 0.2 mm in regard to the optical axis.

With continuous reference to FIG. 10, FIG. 17A shows a cross-sectional view and FIG. 17B shows a top view of device 5. FIG. 17B illustrates device 5 configured with a plurality of markers 108 disposed on the top surface of the rigid component 109.

Figure 18:
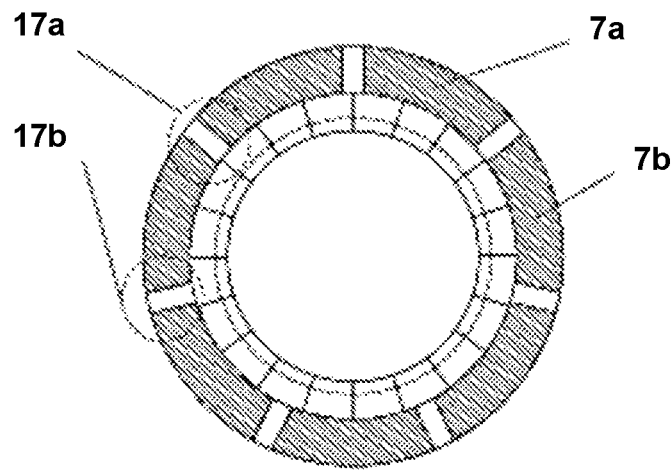
FIG. 18 is a top view of the device showing a plurality of gaps disposed along the circumference of a flexible component thereby dividing the flexible component into plurality of discontinuous sections.

With continuous reference to FIG. 10, FIG. 18 shows a top view of device 5 configured with a plurality of gaps, represented by 17a and 17b, disposed along the circumference of a flexible component 7 to improve flexibility. The gaps divide the flexible component 11 into plurality of discontinuous sections, represented by 7a and 7b and help improve flexibility of the flexible component to accommodate flexibility and dynamic structure of an eye.

Figure 19A:
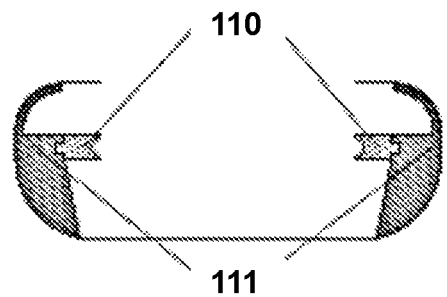
FIGS. 19A-19B are cross-sectional views of the device showing a rigid component constructed of an inner part that secures the optics and/or haptics of an intraocular lens and an outer part that holds the inner part in position.
Figure 19B:
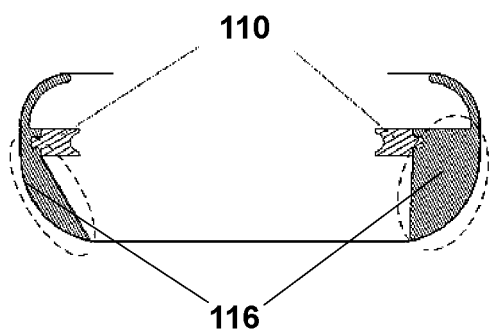

With continuous reference to FIG. 10, FIGS. 19A and 19B are cross-sectional views of the device 5. FIG. 19A is a cross-sectional view of a device 5 configuration where, the rigid component 9 is constructed of two parts, an inner part 110 and an outer part 111, which are essentially concentric and capable of relative rotation of one with respect to the other. The inner part secures the optics and/or haptics of an intraocular lens which can be rotated about the axis of symmetry of the ring-shaped device to bring the lens optics to the desired orientation. The outer part 111 holds the inner part in position and may be rotated with respect to the inner part.

FIG. 19B is a cross-sectional view of a device 5 configuration wherein, the rigid component 9 is constructed of two parts, an inner part 110 and an outer part 116, which are non-coaxial or non-concentric and capable of relative rotation of one with respect to the other. The inner part secures the optics and/or haptics of an intraocular lens which can be rotated about the axis of symmetry of the ring in order to bring the lens optics to the desired orientation. The outer part 116 holds the inner part in position and may be rotated with respect to the inner part. The non-coaxial configuration does not prevent free rotation and is beneficial for some eyes with special conditions.

Figures 20A, 20B:
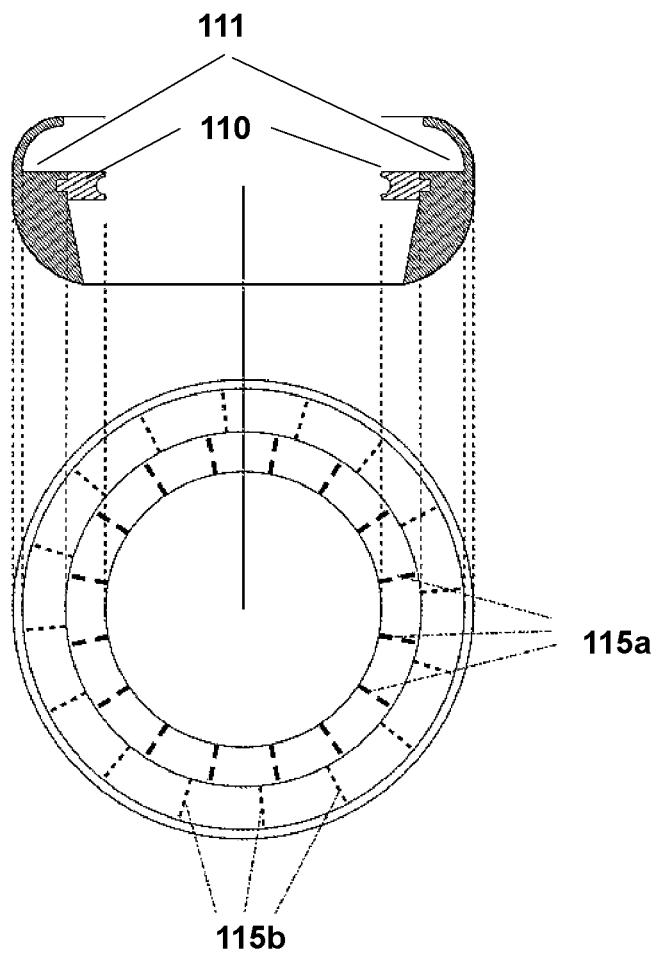
FIGS. 20A-20B show a cross-sectional and a top view of the device.

With continuous reference to FIGS. 10, 19A and 19B, FIGS. 20A and 20B show different views of the device 5. FIG. 20A is a cross-sectional view of a device 5 configuration where the rigid component 9 has an inner part 110 and a concentric outer part 111 (or non-concentric outer part 116, not shown).

FIG. 20B is a top view of the device showing a plurality of markers 115a disposed at the distal end of the inner part and a plurality of markers 115b disposed at the distal end of the outer part.

Figure 21:
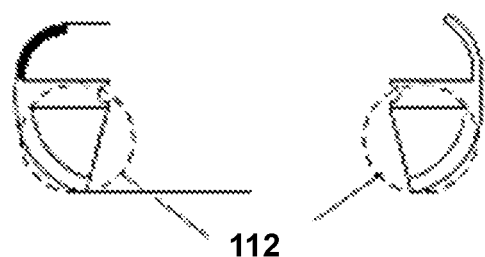
FIG. 21 is a cross-sectional view of the device showing a rigid component with openings to reduce total volume of the device without losing rigidity.

With continuous reference to FIG. 10, FIG. 21 shows a cross-sectional view of a device 5 configuration wherein the rigid component 9 has openings 112 to reduce the total volume of the device without losing rigidity.

Figure 22:
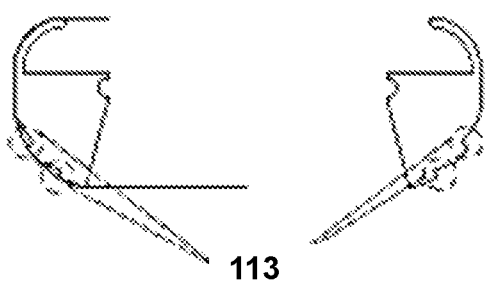
FIG. 22 is a cross-sectional view of the device showing a rigid component configured at a proximal end to prevent post-capsular opacification.

With continuous reference to FIG. 10, FIG. 22 shows a cross-sectional view of a device 5 configuration wherein the rigid component 9 has sharp or tapered edges 113 at the proximal end to prevent post-capsular opacification, thereby avoiding decreased visual acuity, impaired contrast sensitivity, and glare disability commonly associated with cataract patients.

Figure 23:
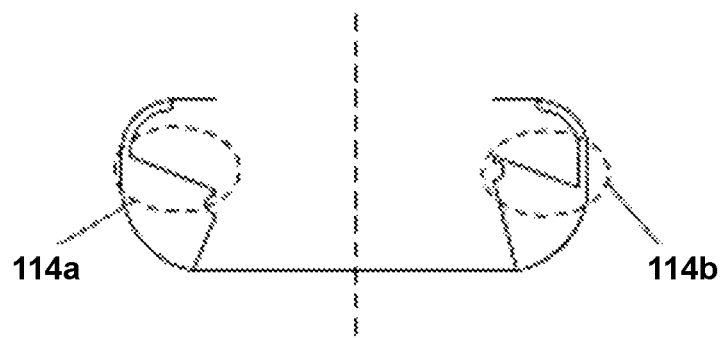
FIG. 23 is a cross-sectional view of the device showing a distal end of a rigid component configured at an angle in relation to an anterior surface of the natural lens capsule when fitted inside.

With continuous reference to FIG. 10, FIG. 23 shows a cross-sectional view of a device 5 configuration wherein a distal end of the rigid component 9 is at an angle 114 in relation to an anterior surface of the natural lens capsule when fitted inside.

Figure 24:
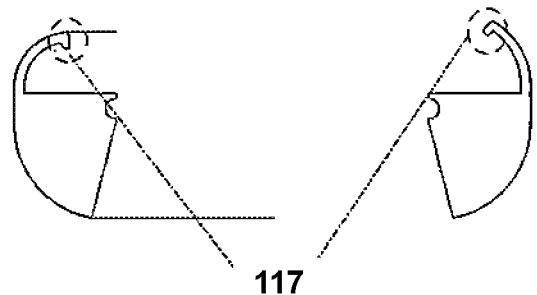
FIG. 24 is a cross-sectional view of the device showing a ledge formed on an inner surface at the distal end of the ring-shaped flexible component.

FIG. 24 shows a cross-sectional view of device 5, where a ledge 117 is formed at the distal end of the ring-shaped flexible component. The ledge receives and secures the haptics of an intraocular lens.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Also, the terms in the claims have their plain, ordinary meaning unless otherwise explicitly and clearly defined by the patentee. sed to secure haptics thereof.

What is claimed is:

1. A prosthetic capsular device for reconstructing a natural lens capsule of an eye after a cataract surgery, the device comprising a housing configured to receive an intraocular lens (IOL), the housing comprising:
   a ring-shaped rigid component comprising:
      a substantially planar distal end, a curved proximal end,
         a circumferential capsular-engaging outer wall extending from said proximal end to said distal end, and a circumferential inner wall extending from said proximal end to said distal end, the proximal end configured to lie against a Wieger's ligament in the eye when the prosthetic capsular device is fitted within the natural lens capsule of the eye;
      an anterior central opening defined at said distal end, the anterior central opening having a perimeter capable of allowing insertion of an intraocular lens;
      a posterior central opening defined at said proximal end;

a groove disposed circumferentially on the circumferential inner wall of the ring-shaped rigid component; and a ring-shaped flexible component consisting of:
  a proximal end that is formed on the distal end of the rigid component;
  a distal end that is a free end extending anteriorly and away from the rigid component; and
  a ledge formed at the distal end thereof;

wherein either the groove and the ledge receive haptics of the intraocular lens when the prosthetic capsular device is fitted within the natural lens capsule of the eye;

wherein the ring-shaped rigid component is asymmetric circumferentially with respect to the flexible component;

wherein the ring-shaped rigid component is substantially concentric with the ring-shaped flexible component;

wherein the ring-shaped rigid component comprises a thickness from 0.1 mm to 2 mm, wherein the ring-shaped flexible component comprises a thickness from 0.05 mm to 1.5 mm, and wherein the thickness of the ring-shaped flexible component is less than the thickness of the ring-shaped rigid component;

wherein the proximal and distal ends of the flexible component comprise capsular-engaging surfaces sized and configured to flexibly fit against an inner surface of the natural lens capsule of the eye;

wherein the capsular-engaging surfaces of the ring-shaped flexible component are continuous with the circumferential capsular-engaging outer wall of the ring-shaped rigid component; and wherein the ring-shaped flexible component is sized and configured to flex away from the ring-shaped rigid component when ciliary muscles are relaxed and zonules are tense, and sized and configured to flex toward the ring-shaped rigid component when the ciliary muscles are contracted and the zonules are relaxed.

2. The device of claim 1, wherein the groove is continuous circumferentially.

3. The prosthetic capsular device of claim 1, wherein the ring-shaped rigid component is substantially perpendicular in relation to an anterior surface of the natural lens capsule when the prosthetic capsular device is fitted within the natural lens capsule of the eye.

4. The prosthetic capsular device of claim 1, wherein the distal end of the ring-shaped rigid component is disposed at an angle to an anterior surface of the natural lens capsule when fitted inside.

5. The device of claim 1, wherein the ring-shaped rigid component and the ring-shaped flexible component are sized and configured to form an angle from about 2 degrees to about 90 degrees as the natural lens capsule contracts and relaxes when the prosthetic capsular device is fitted within the natural lens capsule of the eye.

6. The device of claim 1, wherein the ring-shaped rigid component and the ring-shaped flexible component are independently made of a silicon, an acrylic, a poly (methyl methacrylate), a hydrogel, or a combination thereof.

* * * * *